United States Patent
Watanabe et al.

(10) Patent No.: US 9,205,004 B2
(45) Date of Patent: Dec. 8, 2015

(54) TAMPON INCLUDING A RECESSED PART AND METHOD FOR MANUFACTURING THEREOF

(75) Inventors: Hitoshi Watanabe, Kagawa (JP); Koichi Yamaki, Kagawa (JP); Akie Kikuchi, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 990 days.

(21) Appl. No.: 13/318,394

(22) PCT Filed: May 11, 2010

(86) PCT No.: PCT/JP2010/057958
§ 371 (c)(1),
(2), (4) Date: Jan. 3, 2012

(87) PCT Pub. No.: WO2010/131651
PCT Pub. Date: Nov. 18, 2010

(65) Prior Publication Data
US 2012/0101467 A1    Apr. 26, 2012

(30) Foreign Application Priority Data
May 15, 2009  (JP) ................. 2009-119153

(51) Int. Cl.
*A61F 13/15* (2006.01)
*A61F 13/20* (2006.01)
(52) U.S. Cl.
CPC ............. *A61F 13/20* (2013.01); *A61F 13/2085* (2013.01)

(58) Field of Classification Search
CPC ............ A61F 2013/15; A61F 2013/20; A61F 2013/45; A61F 2013/4587; A61F 2013/15365; A61F 2013/15382
USPC .................. 604/385.17, 385.18, 904, 385.101
See application file for complete search history.

(56) References Cited

U.S. PATENT DOCUMENTS

| | | | |
|---|---|---|---|
| 2,386,590 A | | 10/1940 | Calhoun |
| 2,499,414 A | * | 3/1950 | Rabell ........................... 604/377 |
| 3,618,605 A | * | 11/1971 | Glassman ..................... 604/286 |
| 3,815,601 A | | 6/1974 | Schaefer |
| 4,018,225 A | * | 4/1977 | Elmi ............................. 604/369 |
| 4,335,720 A | | 6/1982 | Glassman |
| 5,634,248 A | * | 6/1997 | McNelis et al. ................. 28/118 |
| 5,659,934 A | * | 8/1997 | Jessup et al. .................... 28/120 |
| 7,070,585 B2 | * | 7/2006 | Jensen ...................... 604/385.17 |

(Continued)

FOREIGN PATENT DOCUMENTS

| | | |
|---|---|---|
| CN | 1874741 A | 12/2006 |
| DE | 2324882 A1 | 11/1974 |

(Continued)

OTHER PUBLICATIONS

International Search Report for PCT/JP2010/057958 mailed Jun. 15, 2010.

(Continued)

*Primary Examiner* — Michelle M Kidwell
(74) *Attorney, Agent, or Firm* — Hauptman Ham, LLP

(57) ABSTRACT

A tampon that has an absorbent body that absorbs a bodily fluid and that is to be inserted into a body cavity along a central axis of the absorbent body, wherein a leading end part in an inserting direction of the absorbent body includes a recessed part including a position of the central axis.

8 Claims, 7 Drawing Sheets

(56) References Cited

U.S. PATENT DOCUMENTS

| | | | |
|---|---|---|---|
| 7,387,622 B1* | 6/2008 | Pauley et al. | 604/385.18 |
| 8,029,485 B2* | 10/2011 | Jensen | 604/385.17 |
| 8,777,916 B2* | 7/2014 | Van Ingelgem et al. | 604/385.17 |
| 2003/0139709 A1 | 7/2003 | Gehling | |
| 2004/0030280 A1 | 2/2004 | Mercier | |
| 2005/0096620 A1 | 5/2005 | Awolin et al. | |
| 2005/0113780 A1 | 5/2005 | Gatto et al. | |
| 2008/0275417 A1 | 11/2008 | Gilbert et al. | |
| 2011/0238028 A1* | 9/2011 | Smet | 604/385.17 |
| 2014/0012221 A1* | 1/2014 | Henson | 604/385.17 |

FOREIGN PATENT DOCUMENTS

| | | |
|---|---|---|
| JP | 47-44897 A | 12/1972 |
| JP | 53-111696 U | 9/1978 |
| JP | 53-144294 U | 11/1978 |
| JP | 57-37341 B2 | 8/1982 |
| JP | 57-160458 A | 10/1982 |
| JP | 62-47543 B2 | 10/1987 |
| JP | 2007-527274 A | 9/2007 |
| JP | 2007-529237 A | 10/2007 |
| JP | 4125377 B2 | 7/2008 |
| KR | 10-2005-0032531 A | 4/2005 |
| WO | 2005051270 A2 | 6/2005 |

OTHER PUBLICATIONS

CN First Office Action (English language) dated Apr. 3, 2013 (2 pages).
Office Action issued Feb. 6, 2014, corresponds to European patent application No. 10774908.7.
Office Action with (English language) corresponding to PCT/JP2010/057958 dated Apr. 22, 2013 (6 pages).
Office Action mailed Dec. 10, 2013, corresponds to Japanese patent application No. 2009-119153.
Office Action mailed Dec. 26, 2013, corresponds to Chinese patent application No. 201080021160.4.

* cited by examiner

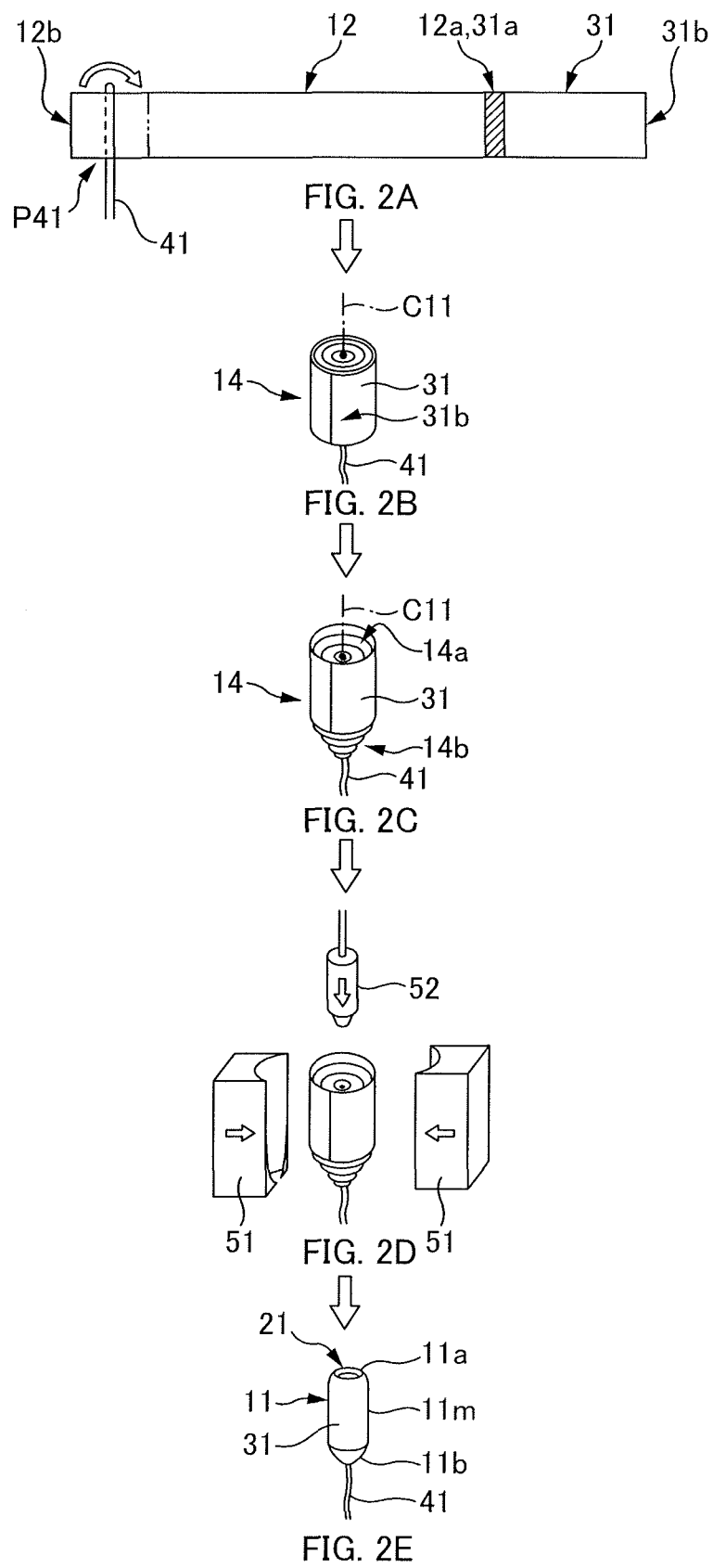

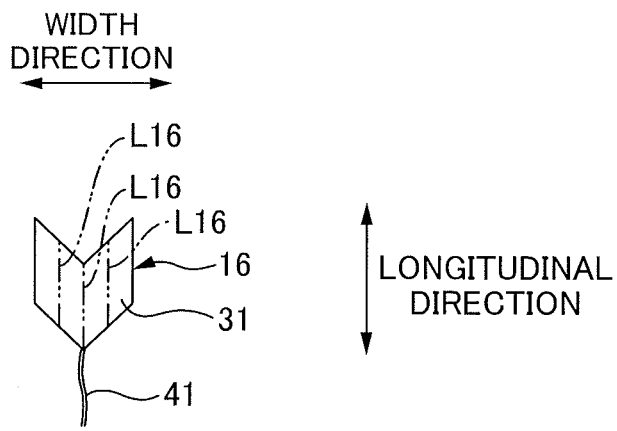
FIG. 4A
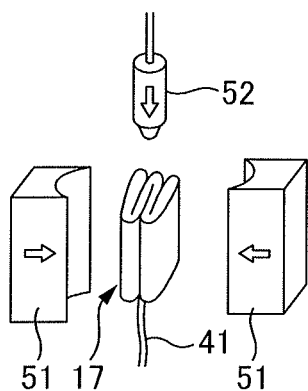
FIG. 4B
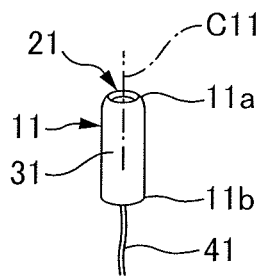
FIG. 4C

TAMPON INCLUDING A RECESSED PART AND METHOD FOR MANUFACTURING THEREOF

RELATED APPLICATIONS

The present application is A National Phase of International Application Number PCT/JP2010/057958, filed May 11, 2010 and claims priority from, Japanese Application Number 2009-119153, filed May 15, 2009.

TECHNICAL FIELD

The present invention relates to a tampon and method for the manufacturing thereof.

BACKGROUND ART

Tampons are known as a sanitary product having an absorbent body that is inserted into a body cavity such as a vaginal cavity and absorbs bodily fluid such as menstrual blood. As an example of the absorbent body, for the purpose of smoothly inserting the absorbent body into the body cavity there is an absorbent body having a top end shape that tapers off in an inserting direction as shown in FIG. 8 (refer to PTL 1).

CITATION LIST

Patent Literature

PTL 1: JP-T-2007-529237

SUMMARY OF INVENTION

Technical Problem

In the case of an absorbent body 111 having such a tapered shape, however, it is hard to receive a flow of the bodily fluid inside the body cavity at a front face thereof. That is, because of the leading end part 111a having the tapered shape, the bodily fluid is guided into between an inner wall face (a circumferential wall face) of the body cavity and a lateral face 111s of the absorbent body 111, and thus easily runs out of the body by running down therebetween. Here, the bodily fluid is absorbed from the lateral face 111s of the absorbent body 111 in the process of running down between the inner wall face of the body cavity and the lateral face 111s; however, in the case where the amount of the bodily fluid is too large, the lateral face 111s cannot fully absorb the bodily fluid and as a result, there is a possibility of the bodily fluid leaking out of the body and soiling an undergarment, etc.

Also, the bodily fluid gradually penetrates from the outside to the inside of the absorbent body 111 in a radial direction when absorbing the bodily fluid from the lateral face 111s of the absorbent body 111, therefore it is hard for the bodily fluid to reach parts in the vicinity of a central axis C111 in the absorbent body 111. That is, it is hard for the parts in the vicinity of the central axis C111 to contribute to the absorption of the bodily fluid. Thus, there is a fear that the absorption capacity corresponding to the volume of the absorbent body 111 cannot be used efficiently.

Further, regarding the absorption from the lateral face 111s of the absorbent body 111, in a case where the flow amount distribution of the bodily fluid is extremely biased with respect to a circumferential direction Dc of the body cavity, the absorbent body 111 does not swell uniformly with respect to the circumferential direction Dc, that is, a part with the large amount flow of bodily fluid will selectively swell and deform in the circumferential direction Dc. Because of this, there is a fear that the absorbent body 111 will bend, or will project partially and thereby cause a sense of discomfort while using a tampon 110.

The present invention was made in view of the foregoing issue, and it is an object thereof to provide a comfortable tampon that prevents body fluid such as menstrual blood from leaking out of a body, and a method of manufacturing such a tampon.

Solution to Problem

A main aspect of the invention for solving the foregoing issue is a tampon that has an absorbent body that absorbs a bodily fluid and that is to be inserted into a body cavity along a central axis of the absorbent body, wherein:

a leading end part in an inserting direction of the absorbent body includes a recessed part including a position of the central axis.

Another aspect of the invention is a method of manufacturing a tampon that has an absorbent body formed of an absorbent material that absorbs a bodily fluid as a main material and that is to be inserted into a body cavity along a central axis of the absorbent body, the method including:

forming a recessed part including a position of the central axis in a leading end part in an inserting direction of the absorbent material; and molding the absorbent body by compressing the absorbent material.

Advantageous Effects of Invention

According to the present invention, a comfortable tampon that prevents body fluid such as menstrual blood from leaking out of a body and a method of manufacturing such tampon can be provided.

BRIEF DESCRIPTION OF DRAWINGS

FIGS. 2A to 2E are explanatory diagrams of a method of manufacturing the tampon 10 of the first embodiment.

FIGS. 4A to 4C are explanatory diagrams of a method of manufacturing the tampon 10 of the second embodiment.

DESCRIPTION OF EMBODIMENTS

Figure 1A:
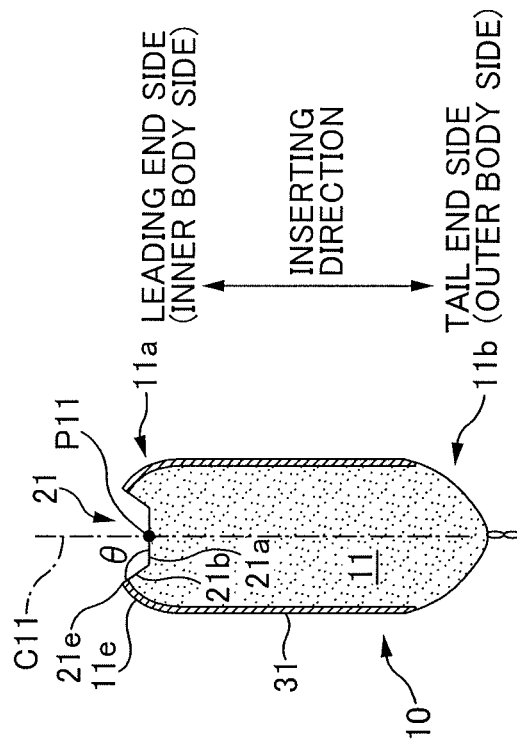
FIG. 1A is a perspective view of a tampon 10 according to a first embodiment.

At least the following matters will become clear through the description of the present specification and the accompanying drawings.

A tampon that has an absorbent body that absorbs a bodily fluid and that is to be inserted into a body cavity along a central axis of the absorbent body, wherein:

a leading end part in an inserting direction of the absorbent body includes a recessed part including a position of the central axis.

According to this tampon, the recessed part on the leading end part is formed by including the position of the central axis of the absorbent body. The central axis of the absorbent body substantially coincides with the center of the body cavity, at the time of inserting the absorbent body into the body cavity. Thus, the recessed part can receive the bodily fluid running inside the body cavity at an approximately front face of the body cavity. The recessed part functions as a weir with respect to the received bodily fluid and temporarily holds the received bodily fluid, and during such temporary holding, the bodily fluid penetrates into the absorbent body from a bottom face of the recessed part and is thereby absorbed. In this way, the amount of the bodily fluid that runs out of the body by running down between an inner wall face of the body cavity and a lateral face of the absorbent body can be reduced, and as a result, the leakage of the bodily fluid to the outside of the body can be prevented efficiently.

Also, the recessed part includes the central axis of the absorbent body, and therefore the bodily fluid held in the recessed part spreads radially and penetrates toward the outside from the central axis on the whole. That is, parts in the vicinity of the central axis of the absorbent body can contribute to the absorption of the bodily fluid, and by adding the absorption from the lateral face of the absorbent body, approximately the whole area of the absorbent body can be used for the absorption of the bodily fluid. Thus the absorption capacity corresponding to the volume of the absorbent body can be fully used.

Further, because of the radial spread of the bodily fluid from the central axis as mentioned above, the absorbent body is swelled and deformed approximately-uniformly in its circumferential direction, that is, the absorbent body swelling and deforming unequally in the circumferential direction will be suppressed. Thereby, the absorbent body deforming by bending and deforming by partially projecting during use is reduced.

In the tampon, it is preferable that the absorbent body is formed of a hydrophilic fiber as a main material, and the hydrophilic fiber is exposed in at least a partial area on a surface of the recessed part.

According to this tampon, the bodily fluid received by the recessed part is sucked into the absorbent body smoothly by the hydrophilic fiber exposed in at least a partial area on the recessed part, and spreads and penetrates inside the absorbent body through the hydrophilic fiber. Thus, absorption speed of the bodily fluid can be increased.

In the tampon, it is preferable that the partial area includes the position of the central axis.

According to this tampon, the bodily fluid received by the recessed part is guided to the central axis of the absorbent body smoothly by the hydrophilic fiber exposed in the partial area of the recessed part and penetrates along the central axis direction to the inside of the absorbent body. Thus, the part in the vicinity of the central axis can reliably contribute to the absorption of the bodily fluid.

In the tampon, it is preferable that the absorbent body is formed of the hydrophilic fiber as the main material, a tail end part in the inserting direction of the absorbent body has a tapered shape, and the hydrophilic fiber is exposed in at least a partial area on a surface of the tail end part.

According to this tampon, even in the case where the bodily fluid reaches the tail end part of the absorbent body by running down between the inner wall face of the body cavity and the lateral face of the absorbent body, the bodily fluid is smoothly sucked and captured inside the absorbent body by the hydrophilic fiber exposed in the partial area on the tail end part. In this way, the leakage of the bodily fluid to the outside of the body can be prevented.

Also, because the tail end part is tapered, the frictional resistance at the time of pulling out the absorbent body from the body cavity becomes small and as a result, the physical strain can be lessened.

In the tampon, it is preferable that the hydrophilic fiber is exposed in at least the partial area on the surface of the recessed part, and a lateral face part of the absorbent body positioned between the recessed part and the tail end part is covered with a covering material that has higher hydrophobicity than the hydrophilic fiber.

According to this tampon, the lateral face part of the portion that easily contacts the inner wall face of the body cavity in the absorbent body is covered with the hydrophobic covering material, and therefore the absorbent body sticking to the inner wall face can be suppressed and the physical strain that accompanies an insertion and a pulling-out operation of the absorbent body is lessened.

Also, in the above-mentioned configuration, the hydrophobic covering material covers parts except the recessed part and the tail end part on the surface of the absorbent body. Thus, the covering material does not block the guidance of the bodily fluid performed by the hydrophilic fiber exposed from the recessed part and the tail end part, and the hydrophilic fiber in the recessed part and the tail end part can smoothly suck the bodily fluid into the absorbent body.

Also a method of manufacturing a tampon that has an absorbent body formed of an absorbent material that absorbs a bodily fluid as a main material and that is to be inserted into a body cavity along a central axis of the absorbent body, the method including:

forming a recessed part including a position of the central axis in a leading end part in an inserting direction of the absorbent material; and molding the absorbent body by compressing the absorbent material.

According to this method of manufacturing a tampon, the tampon formed with the recessed part that realizes the above-mentioned function and effect can be certainly manufactured.

In the method of manufacturing a tampon, it is preferable that in forming the recessed part, the recessed part is formed by compressing a portion that corresponds to the leading end part of the absorbent material along the central axis with a pressing member.

According to this method of manufacturing a tampon, the tampon formed with the recessed part that realizes the above-mentioned function and effect can be easily manufactured.

In the method of manufacturing a tampon, it is preferable that in forming the recessed part, the recessed part in the leading end part is formed by pulling out a tail-end-side part in the inserting direction of the absorbent material along the central axis.

According to this method of manufacturing a tampon, the recessed part can be formed without using a compression method, and even in the case of using the compression method the degree of compression can be set small and thereby can form the recessed part with a material density being low. Due to the recessed part having a low material density, the absorbency (sucking property) of the recessed part for absorbing the bodily fluid into the absorbent body can be improved. As a result, retention of the bodily fluid on the recessed part can be suppressed.

Also, by pulling out the tail end part, the surface area of the absorbent body will be increased at least for the pulled out amount. Thus, the capability of absorbing the bodily fluid can be improved without increasing the amount (weight) of the absorbent material at all.

In the method of manufacturing a tampon, it is preferable that the absorbent material is a sheet-shaped member, and in forming the recessed part, the recessed part on the leading end part is formed by, while rolling up the sheet-shaped member into a roll shape, shifting a part to the central axis side closer to a tail end side in the inserting direction than an outside part thereof in a radial direction.

According to this method of manufacturing a tampon, the recessed part can be formed without using a compression method, and even in the case of using the compression method the degree of compression can be set small and thereby the recessed part with a low material density can be formed.

===First Embodiment===

Figure 1B:
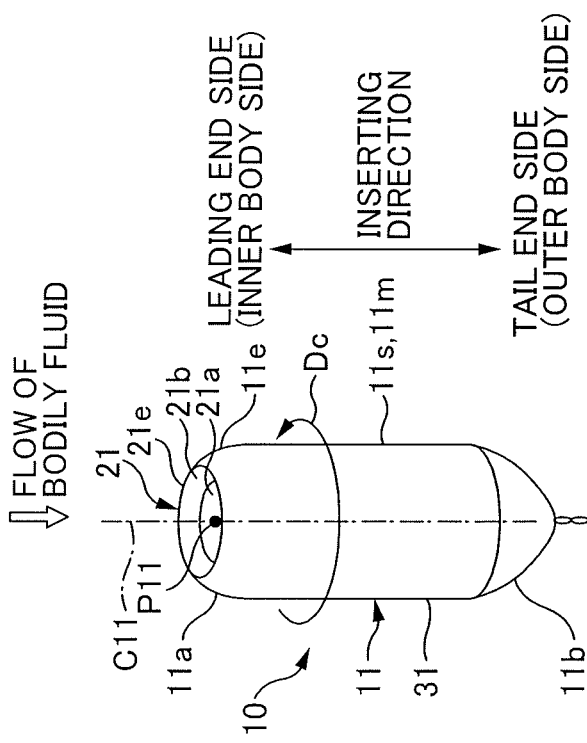
FIG. 1B is a vertical cross-sectional view of the tampon 10 according to the first embodiment.
Figure 1C:
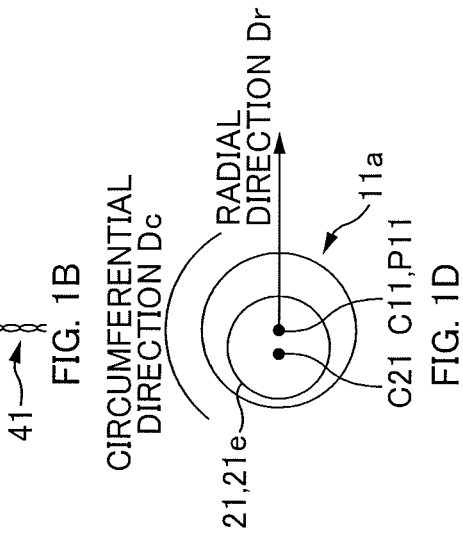
FIG. 1C is an elevational view of the tampon 10 according to the first embodiment.

FIGS. 1A to 1C are explanatory diagrams of a tampon 10 according to a first embodiment. FIG. 1A is a perspective view of the tampon 10. FIG. 1B is a vertical cross-sectional view of the tampon 10. FIG. 1C is an elevational view of the tampon 10.

The tampon 10 has an absorbent body 11 that is to be inserted into a vaginal cavity, that is an example of a body cavity, and a pulling-out cord 41 that becomes a hold at the time of pulling out the absorbent body 11 from inside the vaginal cavity. Hereafter, a side that is inserted into a deep side of the vaginal cavity in an inserting direction of the vaginal cavity is referred to as a leading end side, and an opposite side thereof is referred to as a tail end side.

The absorbent body 11 blocks the vaginal cavity and absorbs bodily fluid such as menstrual blood. For example, the absorbent body 11 is formed with a hydrophilic fiber such as rayon fiber and cotton fiber as a main material and is formed by compressing and molding the main material into a substantially cylindrical shape. The diameter of the absorbent body 11 is from 5 mm to 30 mm, and the length of the absorbent body 11 is from 25 mm to 70 mm. The outer surface thereof is covered with a covering material 31 made of a hydrophobic material such as PETSB (polyethylene terephthalate spunbond nonwoven fabric) except for one part of a leading end part 11a (a recessed part 21 described later) and a tail end part 11b. The covering material 31 reduces the frictional resistance generated when the absorbent body 11 is inserted into or pulled out from the vaginal cavity based on its hydrophobic character. Furthermore, the covering material 31 is not necessary.

The recessed part 21 is formed in the leading end part 11a of the absorbent body 11. The recessed part 21 is formed in a perfect circle shape, and a circle center which is a center C21 of the plane face thereof is concentric with a central axis C11 of the absorbent body 11. Thus, the recessed part 21 is facing a front face of the vaginal cavity and thereby can receive in the front face the menstrual blood running inside the vaginal cavity. While temporarily holding the received menstrual blood, the recessed part 21 absorbs the menstrual blood through a bottom face part 21a or the like to the inside of the absorbent body 11. In this way, the amount of the menstrual blood running down between an inner wall face of the vaginal cavity and a lateral face 11s of the absorbent body 11 can be lessened. As a result, the leakage of the menstrual blood to a part of the vaginal cavity positioned more to the outer side than the absorbent body 11 can be efficiently prevented.

However, it is not always necessary for the center of the plane face C21 of the recessed part 21 to coincide with the central axis C11 of the absorbent body 11 as described above. That is, if the recessed part 21 is formed so as to include a position P11 of the central axis C11 in the leading end part 11a of the absorbent body 11, the recessed part 21 approximately faces the front face of the vaginal cavity and the above-mentioned function and effect can be achieved accordingly.

Here, the reason why the recessed part 21 includes the position P11 of the central axis C11 of the absorbent body 11, and the recessed part 21 faces the front face of the vaginal cavity are considered to be substantially equal in value as mentioned above is as described below.

Figure 1D:
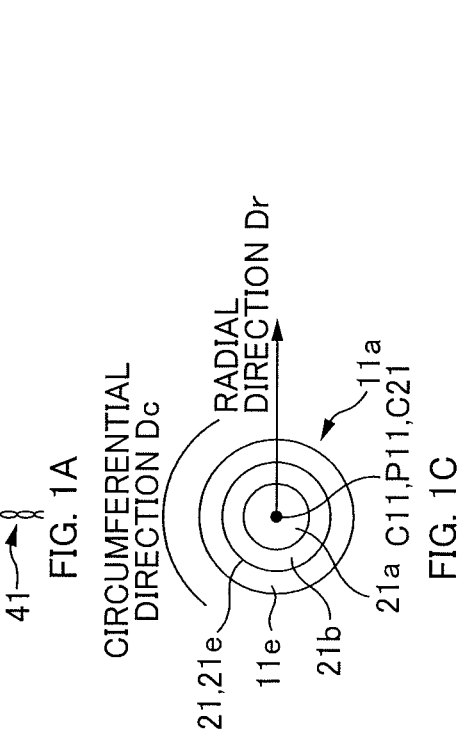
FIG. 1D is an elevational view a tampon 10 of a modified example.

Usually, the absorbent body 11 is inserted into the vaginal cavity along the central axis C11 thereof. Thus, the central axis C11 substantially coincides with the center of the vaginal cavity, and in the case where the recessed part 21 includes the central axis C11 of the absorbent body 11, the recessed part 21 inevitably includes the center of the vaginal cavity, and this is a similar state to the recessed part 21 substantially facing the front face of the vaginal cavity. Therefore, for example, as shown in an elevational view of a modified example of FIG. 1D, the center of the plane face C21 of the recessed part 21 can be decentered from the central axis C11 of the absorbent body 11. By the way, "the central axis C11 of the absorbent body 11" described above can be expressed as "a line made by joining the centers of the plane face of lateral cross sections in a longitudinal direction of the absorbent body 11, the direction of the normal to the lateral cross sections being the longitudinal direction of the absorbent body 11".

Further, if the recessed part 21 includes the central axis C11 of the absorbent body 11, the menstrual blood temporarily held in the recessed part 21 will generally radially spread and penetrate toward the outside from the central axis C11 in a radial direction Dr. That is, in regards to the part in the vicinity of the central axis C11 that is difficult for the menstrual blood to reach when the menstrual blood is absorbed from the lateral face 11s of the absorbent body 11, this part can also reliably contribute to the absorption of the menstrual blood. By adding the absorption from the lateral face 11s of the absorbent body 11, approximately a whole area of the absorbent body 11 can be used in the absorption of the menstrual blood. As a result, fluid absorption capacity corresponding to the volume of the absorbent body 11 can be fully used.

Further, due to the radial spread of the menstrual blood from the central axis C11 as mentioned above, the absorbent body 11 swells and deforms approximately uniformly with respect to its circumferential direction Dc, that is, the absorbent body 11 swelling and deforming unequally in the circumferential direction Dc is suppressed. Thereby, deformation by bending or partially projecting of the absorbent body 11 during use can be reduced.

By the way, as shown in FIGS. 1A and 1B, a circular edge part 21e that forms the outer shape of the recessed part 21 is a peak part of the leading end part 11a of the absorbent body 11. That is, a part lie positioned more to the outer side than the edge part 21e of the recessed part 21 in the leading end part 11a of the absorbent body 11 in the radial direction Dr has a so-called sloping shoulder shape without corner parts such as with curved surfaces that have been chamfered. Thereby, resistance that occurs when inserting the absorbent body 11 into the vaginal cavity is relaxed. The diameter of the edge part 21e is from 0.5 mm to 14 mm for example, and preferably the diameter is from 3 mm to 8 mm. In the case where the latter range is adopted, the menstrual blood running inside the vaginal cavity could be reliably received by the recessed part 21.

Also, the recessed part 21 has the bottom face part 21a in a flat perfect circle shape including the central axis C11 of the absorbent body 11 as a circle center, and a sloping part 21b that connects an outer circumferential edge of the bottom face part 21a and the edge part 21e. The bottom face part 21a is a face that is substantially perpendicular to the central axis C11. The sloping part 21b is a substantially circular cone face in which a narrow angle θ between the sloping part 21b and the bottom face part 21a is from 30 degrees to 150 degrees for example, and preferably is a substantially circular cone face with the narrow angle θ from 45 degrees to 80 degrees. In the case where the latter range is adopted, the edge part 21e becomes an appropriately closed shape to the extent that the menstrual blood running inside the vaginal cavity can be received without any hindrance. In this way, it is possible to achieve both capability of receiving the menstrual blood, and retaining capability of retaining the once received menstrual blood inside the recessed part 21.

The depth of the recessed part 21 (the depth of the bottom face part 21a from the edge part 21e) is from 0.1 mm to 10 mm for example, and is preferably from 0.5 mm to 3 mm. In the case where the latter range is adopted, the edge part 21e of the recessed part 21 functions efficiently as a weir particularly based on the depth of equal to or greater than 0.5 mm. Thereby, the configuration in which the once received menstrual blood is kept from running out to the outside is achieved.

Here, it is preferable that the recessed part 21 is not covered with the hydrophobic covering material 31 mentioned before. That is, as shown in FIG. 1B, it is preferable that the hydrophilic fiber as a main material of the absorbent body 11 is exposed over the entire surface of the recessed part 21. With such a configuration, based on the hydrophilic property of the exposed area, the retained menstrual blood at the slope part 21b and the bottom face part 21a of the recessed part 21 is sucked quickly into the inside of the absorbent body 11 in a direction along the central axis C11 (hereafter, referred to as a central axis direction C11), and retention of the menstrual blood in the recessed part 21 is solved quickly. That is, the recessed part 21 can easily recover to the state where there is no retained menstrual blood and receiving the next menstrual blood is possible. In this way, the capability of receiving the menstrual blood of the recessed part 21 is remarkably improved.

Further, the hydrophilic fiber does not have to be exposed on the entire surface of the recessed part 21, and it can be partly exposed in some area of the recessed part 21. In the case where the hydrophilic fiber is exposed in the partial area of the recessed part 21, it is preferable that the position of the central axis C11 of the absorbent body 11 is included in the partial area. For example, in the example of FIG. 1C, it is preferable that the hydrophilic fiber is exposed in the bottom face part 21a that includes the central axis C11. That is, the slope part 21b can be covered with the covering material 31. In a case where the hydrophilic fiber is exposed in the partial area that includes the central axis C11 of the absorbent body 11, the menstrual blood is preferentially delivered to the part in the vicinity of the central axis C11 inside the absorbent body 11, and thus a zone in which the menstrual blood is not absorbed can be reduced in the part in the vicinity of the central axis C11.

Also, as in an example of FIG. 1B, it is preferable that the hydrophilic fiber as a main material of the absorbent body 11 is exposed on a surface of the tail end part 11b of the absorbent body 11 instead of being covered with the hydrophobic covering material 31. In the example of FIG. 1B, from a viewpoint of relaxing the resistance at the time of pulling out the absorbent body 11 from the vaginal cavity, the outer shape of the tail end part 11b is a tapered shape with the diameter becoming smaller as it goes to the tail end, and the hydrophilic fiber is exposed from the entire surface of this tapered part 11b. With such configuration, even in a case where the menstrual blood reaches the tail end part 11b by running down between the inner wall face of the vaginal cavity and the lateral face 11s of the absorbent body 11, the menstrual blood is absorbed into the tail end part 11b based on the hydrophilic property of the surface of the tail end part 11b. In this way, the leakage of the menstrual blood to the outside of the body can be prevented. However, the hydrophilic fiber does not have to be exposed in the entire surface of the tail end part 11b, that is, an appropriate effect can be achieved also in a case where the hydrophilic fiber is partially exposed in the tail end part 11b.

FIGS. 2A to 2E are explanatory diagrams of a method of manufacturing the tampon 10.

First, as shown in FIG. 2A, for an absorbent material as a main material of the absorbent body 11, a band shaped sheet 12 made of the hydrophilic fiber having a width from 30 mm to 100 mm and a length from 150 mm to 300 mm is formed by cutting out a whole cloth roll or the like. One end part 12a of the band shaped sheet 12 in the longitudinal direction and one end part 31a of the sheet-form covering material 31 having a same width as the band shaped sheet 12 and a length from 50 mm to 200 mm are overlapped by aligning each center in the width direction and are joined by welding and adhesion and the like.

After that, the pulling-out cord 41 is disposed across the band shaped sheet 12 in the width direction on both sides sandwiching both sides of the band shaped sheet 12, and in such state the band shaped sheet 12 is folded at a crossing position P41 where the pulling-out cord 41 crosses the band shaped sheet 12 as a folding position, and another end part 12b of the band shaped sheet 12 in the longitudinal direction overlaps the band shaped sheet 12. The band shaped sheet 12 is rolled up in the longitudinal direction so that the fold position P41 becomes a roll-up core and thereby becomes a roll shape as shown in FIG. 2B. Another end part 31b of the covering material 31 that forms an outer circumference of the roll is joined to an outer circumferential face of the roll by welding and adhesion or the like, whereby a roll body 14 having the diameter from 10 mm to 50 mm is produced.

Further, the covering material 31 of at least a single circuit (a single layer) is present in the outer circumferential face of the roll body 14, that is, the outer circumferential face of the roll body 14 is in a state where the entire circumference thereof is covered with the covering material 31.

Next, as shown in FIG. 2C, a part in the vicinity of a roll-up core C11 of the roll body 14, that is, a part in the vicinity of the central axis C11 of the roll body 14 is pulled out from a side of the pulling-out cord 41 in range from 0 mm to equal to or greater than 40 mm (in range from 5 mm to 25 mm is preferable) along the central axis direction C11. In this way, a projected part 14b having a shape of a bamboo shoot is formed in an end part to the pulling-out cord 41 side in the central axis direction C11. On the other hand, a dented part 14a having a substantially same shape is formed in an end part on the opposite side (corresponds to "forming a recessed part"). Here, these both end parts respectively correspond to the tail end part 11b and the leading end part 11a of the absorbent body 11. That is, after a subsequent press molding, the above mentioned dented part 14a becomes the recessed part 21 that relates to the leading end part 11a, and the above mentioned projected part 14b becomes the tapered part 11b that relates to the tail end part 11b. In addition, the dented part 14a and the projected part 14b are pulled out and thus formed as mentioned above, and therefore they are both not covered with the covering material 31 and they are in a state where the hydrophilic fiber is exposed in the entire surface thereof. Thereby, even after the subsequent press molding, the hydrophilic fiber is to be certainly exposed in the recessed part 21 of the leading end part 11a and the tapered part 11b of the tail end part 11b.

After that, as shown in FIG. 2D, the roll body 14 is sandwiched from both sides by a pair of press molds 51, 51 for lateral parts that approach the outer circumferential face of the roll body 14 from the sides, and thereby compressed into a substantially cylindrical shape. In this way, parts except the leading end part 11a of the absorbent body 11, that are, a middle part 11m and the tail end part 11b of the absorbent body 11 are molded (corresponds to "molding an absorbent body"). On the other hand, at the same time or before-or-after the above, the leading end part 11a of the absorbent body 11 is molded by a press mold 52 (corresponds to a press member) for the leading end part moving along the central axis C11 toward the leading end part 11a and compressing the leading end part 11a in the central axis direction C11 (corresponds to "forming a recessed part" and "molding an absorbent body"). Here, these press molds 51 and 52 have a shape that corresponds to the tapered shape of the tail end part 11b of the absorbent body 11 and the shape of the recessed part 21 on the leading end part 11a and the like respectively. Thereby, the absorbent body 11 having the recessed part 21 and the tapered part 11b as shown in FIG. 2E is molded. In addition, at the same time or right after the press molding, a heating process can be performed for the purpose of fixing the shape of the absorbent body 11 certainly.

On the other hand, in the case of this first embodiment, in the state before being press molded (FIG. 2C) as described before, the dented part 14a is already formed in a portion corresponding to the leading end part 11a, and the projected part 14b is already formed in a portion corresponding to the tail end part 11b in the roll body 14. Therefore, the recessed part 21 and the tapered part 11b can be molded without making the compression amount in the press molding quite large. In this way, the density of fiber distribution can be made low in the recessed part 21 and the tapered part 11b, and as a result, the absorbency of the menstrual blood, especially the menstrual blood of high viscosity (so-called sludgy menstrual blood) can be improved. Furthermore, it is possible to fully omit the press molding for molding the leading end part 11a and perform only the press molding for molding the middle part 11m and the tail end part 11b. Thereby, the density of fiber distribution can be made extremely low in the recessed part 21 and the absorbency thereof can be remarkably improved. Also, in such a case, a structure that is dented in stair-like pattern toward the central axis C11 from the outside to the inside in the radial direction Dr is apt to remain in the recessed part 21, as a vestige of forming the recessed part 21 by pulling-out. Due to such stair-like structure functioning efficiently as a weir, the menstrual blood once received in the recessed part 21 is kept from escaping outside.

Further, the tapered part 11b of the tail end part 11b is molded by pulling it out in a shape of a bamboo shoot, and thus it is possible to increase only the surface area of the hydrophilic fiber of the absorbent body 11 without increasing its total volume (FIG. 2C). Thus, the absorbency of the absorbent body 11 can be improved while maintaining constant the total volume of the hydrophilic fiber related to the absorbent body 11.

Also, in the above description, a method of pulling out the part in the vicinity of the central axis C11 of the roll body 14 after generating the roll body 14 is used as a method of forming the dented part 14a and the projected part 14b of the roll body 14. However, there is no limitation to this and for example, the above-described dented part 14a and the projected part 14b can be formed by gradually shifting the part in the vicinity of the central axis C11 as a roll-up core in the direction along the central axis C11 while rolling up the band shaped sheet 12 into a roll shape, or by rolling up a parallelogram sheet instead of the rectangular band shaped sheet 12. Here, in the latter method of using the parallelogram sheet, the dented part 14a and the projected part 14b can be automatically formed by simply rolling up the parallelogram sheet without performing the pulling out operation in the central axis direction C11.

===Second Embodiment===

Figure 3A:
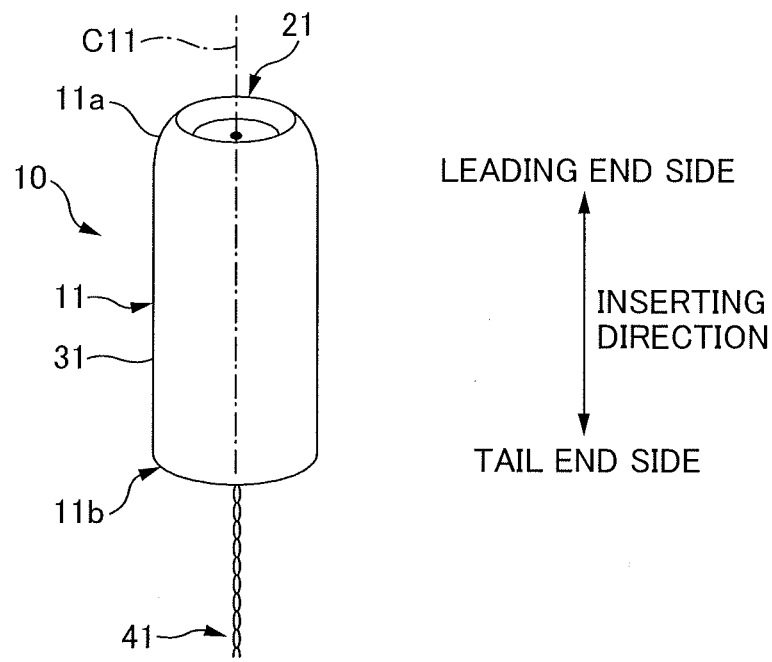
FIG. 3A is a perspective view of a tampon 10 according to a second embodiment.
Figure 3B:
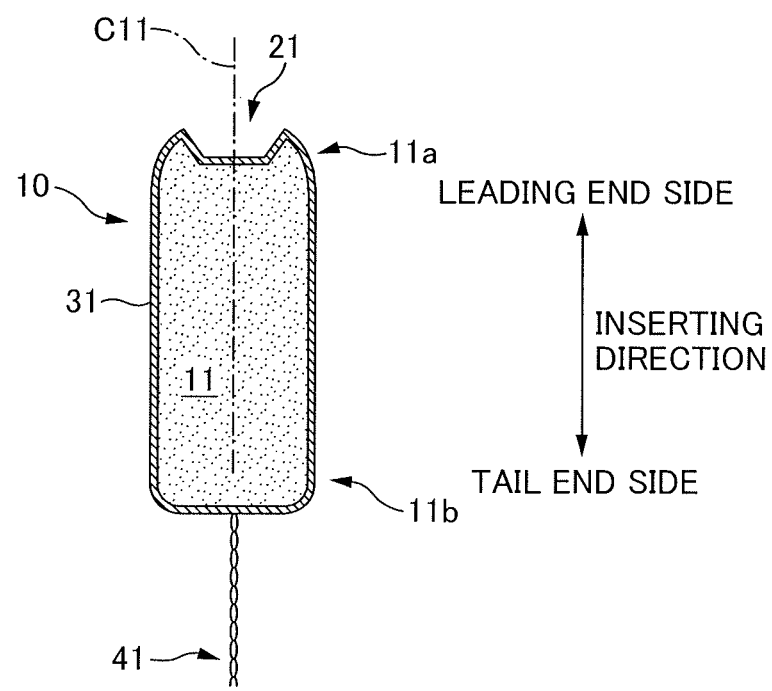
FIG. 3B is a vertical cross-sectional view of the tampon 10 according to the second embodiment.

FIGS. 3A and 3B are explanatory diagrams of the tampon 10 according to a second embodiment. FIG. 3A is a perspective view of the tampon 10 according to the second embodiment. FIG. 3B is a vertical cross-sectional view of the tampon 10 according to the second embodiment.

In the above mentioned first embodiment, the recessed part 21 of the leading end part 11a of the absorbent body 11 and the tail end part 11b are not covered with the hydrophobic covering material 31. However, the recessed part 21 and the tail end part 11b are covered with the hydrophobic covering material 31 in the tampon 10 of the second embodiment, that is, the tampon 10 of the second embodiment differs from the tampon 10 of the first embodiment in respect of the substantially entire surface of the absorbent body 11 being covered by the covering material 31. Also, the above two embodiments differ in respect of the tail end part 11b having a substantially cylindrical shape instead of a tapered shape. Further, the configuration of the second embodiment except the above is substantially the same as that of the first embodiment, so therefore explanation shall be omitted.

FIGS. 4A to 4C are explanatory diagrams of a method of manufacturing the tampon 10 of the second embodiment described above.

First, both sides of a cotton-like sheet formed of the hydrophilic fiber as a main material is covered with the hydrophobic covering material 31 such as PETSB, and the sheet is cut into a feather shape (refer to FIG. 4A). The pulling-out cord 41 is sewn to the center of a feather shaped sheet 16 in the width direction along the longitudinal direction. After that, the feather shaped sheet 16 is folded in a W-shape by folding along three straight lines L16, L16, and L16 along the longitudinal direction.

Next, this W-shaped folded body 17 is sandwiched from both sides (a direction perpendicular to the longitudinal direction) by the pair of press molds 51, 51 for lateral parts as shown in FIG. 4B and thereby compressed into a cylindrical shape. In this way, parts except the leading end part 11a of the absorbent body 11 are molded (corresponds to "molding an absorbent body"). On the other hand, at the same time or before-or-after the above, the leading end part 11a of the absorbent body 11 is molded by being compressed in the longitudinal direction by the press mold 52 for the leading end part moving along the longitudinal direction toward one end part of the folded body 17 in the longitudinal direction (corresponds to "forming a recessed part"). Here, the press mold 52 for the leading end part has the shape corresponding to the shape of the recessed part 21 of the leading end part 11a. Thereby, the absorbent body 11 having the recessed part 21 as shown in FIG. 4C is molded.

Further, according to this method of manufacturing, the absorbent body 11 is molded after being in the state of W-shaped folded body 17 shown in FIG. 4B. Thus, as a vestige of being in such W-shape, cracks that lie along the longitudinal direction (central axis direction C11) remain inside the molded absorbent body 11 in substantially the entire length. Due to these cracks, the penetration of the menstrual blood in the central axis direction C11 of the absorbent body 11 is improved. Thereby, drainage of the recessed part 21 can be improved, and surface recovery thereof is promoted.

Figure 5A:
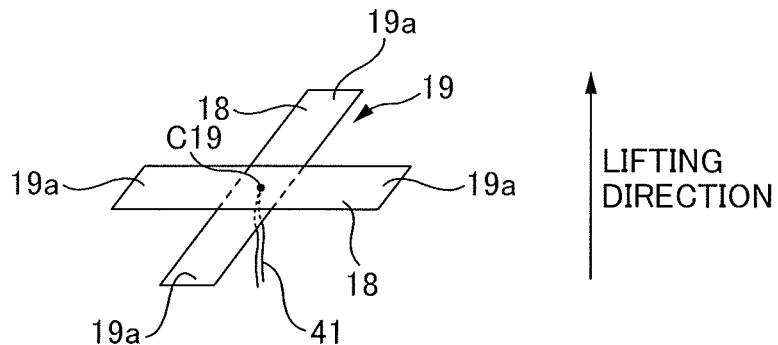
FIGS. 5A to 5C are explanatory diagrams of another method of manufacturing the tampon 10 of the second embodiment.
Figure 5B:
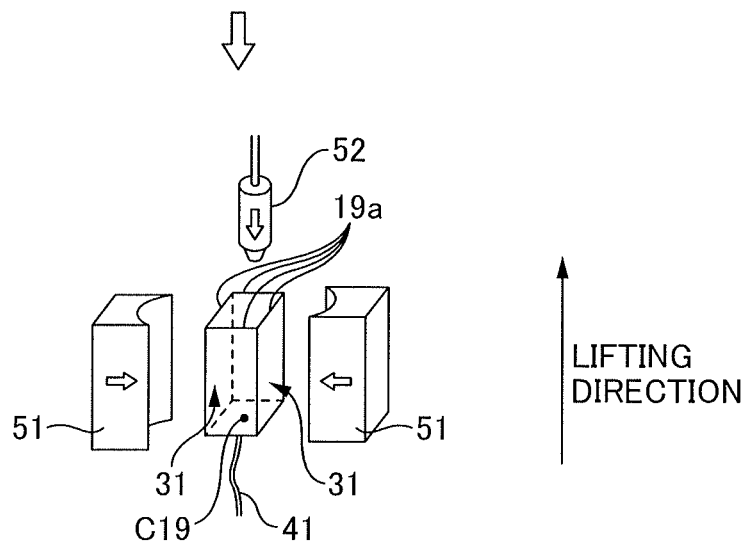
Figure 5C:
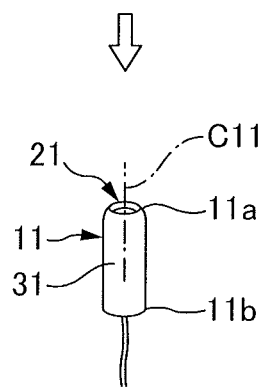

FIGS. 5A to 5C are explanatory diagrams of another method of manufacturing the tampon 10 of the second embodiment.

First, one side of a cotton-like sheet formed of the hydrophilic fiber as a main material is covered with the hydrophobic covering material 31 such as PETSB, and the sheet is cut into a band-shape and thus two of the band-shaped sheets are formed. As shown in FIG. 5A, these band-shaped sheets 18, 18 are overlapped in a cross shape while threading the pulling-out cord 41 into a plane center position C19 of a crossed sheet body 19 and thus fixing it. Then, as shown in FIG. 5B, four end parts 19a of the crossed sheet body 19 are relatively lifted and made to oppose each other with respect to the plane center position C19 so that faces on the covering material 31 side face the outside. The crossed sheet body 19 in such state is sandwiched from both sides by the pair of press molds 51, 51 for lateral parts with the central axis C11 of the absorbent body 11 as a lifting direction, and thereby compressed into a cylindrical shape. In this way, parts except the leading end part 11a of the absorbent body 11 are molded (corresponds to "molding an absorbent body"). On the other hand, at the same time or before-or-after the above, the leading end part 11a of the absorbent body 11 is molded by being compressed in the lifting direction by the press mold 52 for the leading end part moving along the lifting direction toward the end parts of the crossed sheet body 19 (corresponds to "forming a recessed part"). Here, the press mold 52 for the leading end part has the shape that corresponds to the shape of the recessed part 21 on the leading end part 11a, and thereby the absorbent body 11 having the recessed part 21 as in FIG. 5C is molded.

Additionally, it is not necessary to use the covering material 31 in the above mentioned two types of method of manufacturing and when the tampon 10 is manufactured without using the covering material 31, the tampon 10 having the absorbent body 11 in which the hydrophilic fiber is exposed on its entire surface will be manufactured.

===Variation of Recessed Part 21===

Figure 6A:
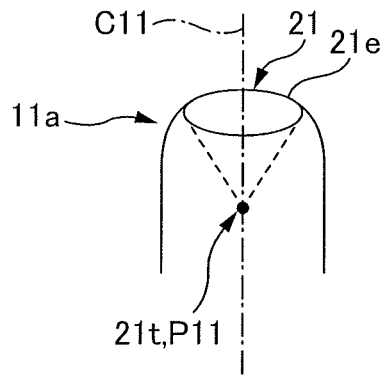
FIGS. 6A to 6C are enlarged views of the leading end part 11a of the absorbent body 11 for explaining variations of a recessed part 21.
Figure 6B:
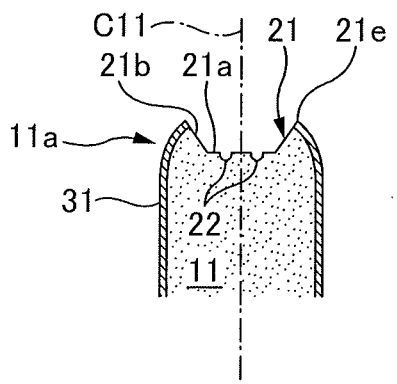
Figure 6C:
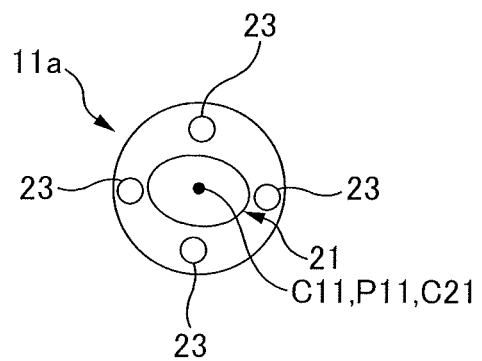

FIGS. 6A to 6C are enlarged views of the leading end part 11a of the absorbent body 11 for explaining variations of the recessed part 21.

In the above mentioned embodiments, the recessed part having a perfect circle shape in planar view and including the central axis C11 of the absorbent body 11 as a circle center is explained as an example of the recessed part 21. However, there is no limitation to this as long as the recessed part 21 is provided on the leading end part 11a of the absorbent body 11 and includes the position P11 of the central axis C11 of the absorbent body 11. For example, the outside shape of the recessed part 21 can be an equilateral polygon such as a regular triangle and a square, or other polygons or a circular shape such as an oval shape (refer to FIG. 6C). Further, it can be a drawing pattern such as a heart shape and a star shape or a letter or the like.

Further, the flat bottom face part 21a is explained as an example of the bottom part of the recessed part 21. However, the bottom part does not necessarily have to be a flat face and for example, as shown in the perspective view of FIG. 6A, the shape of the recessed part 21 can be conical while having a tip 21t thereof as the bottom part. Further, the plurality of the recessed parts 22 can be formed on the bottom face part 21a of the recessed part 21 as shown in the vertical cross-sectional view of FIG. 6B.

Further, as shown in FIG. 6C, extra recessed parts 23 can be provided on the leading end part 11a in addition to the recessed part 21 including the central axis C11 of the absorbent body 11.

===Other Embodiments===

The embodiments according to the present invention were explained as above. However, the present invention is not limited to the above embodiments and the following modifications are possible.

In the above-mentioned embodiments, PETSB was explained as an example of the covering material 31. However, there is no limitation to this and any material is possible as long as it has higher hydrophobicity than the hydrophilic fiber used in the absorbent body 11 as the main material. For example, in the case where the hydrophilic fiber is rayon or cotton fiber, a nonwoven fabric formed of polyester fiber as the main material can be used as the covering material 31.

In the above-mentioned embodiments, the sheet-type covering material 31 was used to make the lateral face of the absorbent body 11 hydrophobic. However there is no limitation to this and a water repellent coating can be performed on the lateral face 11s of the absorbent body 11 in which the hydrophilic fiber as the main material is exposed on the entire surface thereof, and thus provide hydrophobic property to the lateral face 11s of the absorbent body 11.

In the above-mentioned embodiments, the substantially cylindrical shape is explained as an example of the shape of the absorbent body 11, however, the lateral cross-sectional shape of the absorbent body can be a regular circle shape or an oval shape. Further, the absorbent body 11 can be a polygonal prism in which the lateral cross-sectional shape thereof is an equilateral polygon.

Figure 7:
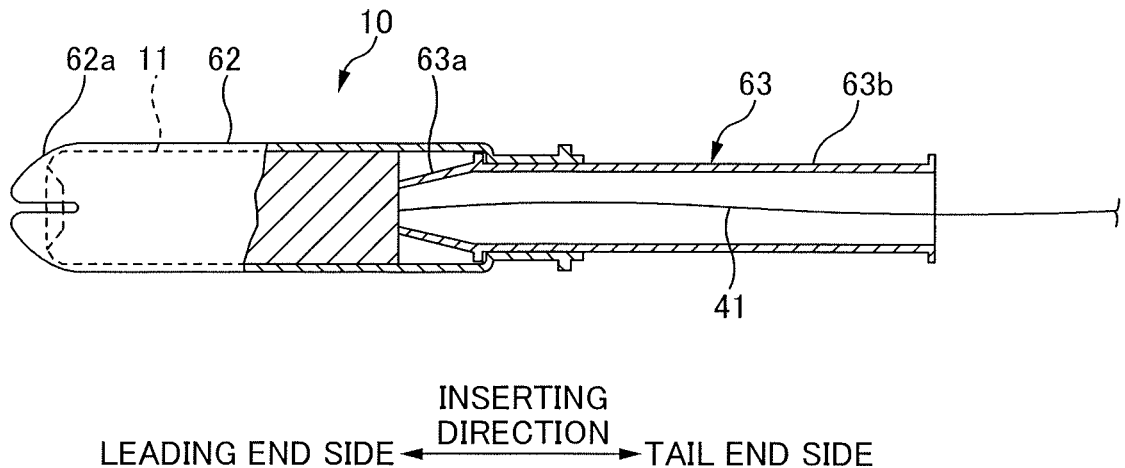
FIG. 7 is a partially-cross-sectional lateral view of the tampon 10 including an applicator 61.
Figure 8:
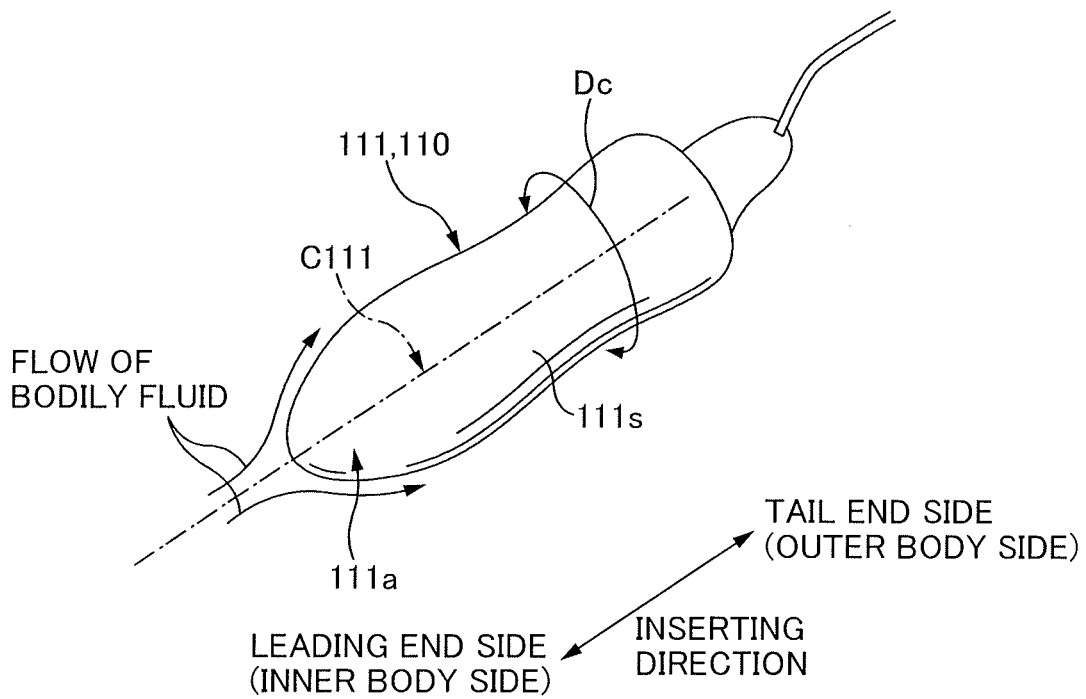
FIG. 8 is a perspective view of a conventional tampon 110.

In the above-mentioned embodiments, an applicator was not explained as an example, however, the applicator can be included. FIG. 7 shows a partially-lateral cross-sectional view of the tampon 10 including an applicator 61. The applicator 61 is an aid used when inserting the absorbent body 11 into the vaginal cavity and the applicator has an outer cylinder 62 and an inner cylinder 63 as shown in FIG. 7. The outer cylinder 62 and the inner cylinder 63 are both formed by injection molding using a resin such as polyethylene. The absorbent body 11 is accommodated in the leading end side of the outer cylinder 62, and a leading end part 63a of the inner cylinder 63 is accommodated in the tail end side of the outer cylinder 62, and a part 63b except the leading end part 63a in the inner cylinder 63 is projected outward from the tail end of the outer cylinder 62. Thus, at the time of using the tampon 10, a leading end part 62a of the outer cylinder 62 is inserted into the vaginal cavity, and by pushing the inner cylinder 63 into the outer cylinder 62 during such state, the absorbent body 11 is pushed out from the leading end part 62a of the outer cylinder 62 and thereby inserted into the vaginal cavity. After inserting the absorbent body 11 the applicator 61 is pulled out from the vaginal cavity.

Reference Signs List 10 tampon, 11 absorbent body, 11a leading end part, 11b tail end part (part that tapers off), 11e part positioned to the outer side, 11m middle part, 11s lateral face, 12 band shaped sheet (absorbent material), 12a one end part, 12b another end part, 14 roll body, 14a dented part, 14b projected part, 16 feather shaped sheet, 17 folded body, 18 band shaped sheet, 19 crossed sheet body, 19a end part, 21 recessed part, 21a bottom face part, 21b slope part, 21e edge part, 21t tip, 22 recessed part, 23 covering material, 31a one end part, 31b another end part, 41 pulling-out cord, 51 press molds for lateral parts, 52 press mold for leading end part (press member), 61 applicator, 62 outer cylinder, 62a leading end part, 63 inner cylinder, 63a leading end part, 63b part except leading end part, Dc circumferential direction, Dr radial direction, C11 central axis (central axis direction, roll-up core), C19 plane center position, C21 center of plane face, L16 straight line, P11 position of central axis, P41 crossing position.

The invention claimed is:

1. A tampon, comprising:
an absorbent body configured to absorb a bodily fluid and adapted to be inserted into a body cavity of a wearer along a central axis of the absorbent body, and
a covering material,
wherein
the absorbent body has
a leading end part,
a tail end part, and
a middle part between the leading end part and the tail end part in an inserting direction of the absorbent body,
the leading end part includes a recessed part including a position of the central axis,
the tail end part has a tapered shape,
the absorbent body is a roll body of a sheet member,
a part of the roll body is pulled out along the central axis to define the tapered shape of the tail end part such that an opposite part of the roll body is pushed in along the central axis to define the recessed part of the leading end part,
the leading end part having the recessed part is not press-molded,
the middle part and the tail end part are press-molded,
the recessed part is dented in a stair-shaped pattern from outside to inside in a radial direction of the absorbent body,
the absorbent body comprises a hydrophilic fiber as a main material of the absorbent body,
the hydrophilic fiber is exposed on a surface of the recessed part and on a surface of the tail end part, and
a lateral face of the middle part is covered with the covering material that has higher hydrophobicity than the hydrophilic fiber.

2. The tampon according to claim 1, wherein the surface of the recessed part includes the position of the central axis.

3. The tampon according to claim 1, wherein
the covering material, that has higher hydrophobicity than the hydrophilic fiber, does not cover the recessed part and the tail end part.

4. A method of manufacturing a tampon that has an absorbent body formed of an absorbent material configured to absorb a bodily fluid, and a covering material, said absorbent body being adapted to be inserted into a body cavity of a wearer along a central axis of the absorbent body, the method comprising:
forming a sheet member into a roll body to obtain the absorbent body;
forming a recessed part including a position of the central axis in a leading end part in an inserting direction of the absorbent body;
wherein a part of the roll body is pulled out along the central axis to form a tapered shape in a tail end part in the inserting direction of the absorbent body, such that an opposite part of the roll body is pushed in along the central axis to form the recessed part of the leading end part; and
molding the absorbent body by compressing the absorbent material,
wherein
said molding the absorbent body includes press-molding (i) the tail end part and (ii) a middle part between the leading end part and the tail end part in the inserting direction, without press-molding the leading end part including the recessed part,
the recessed part is dented in a stair-shaped pattern from outside to inside in a radial direction of the absorbent body,
the absorbent body is formed of a hydrophilic fiber as a main material of the absorbent body,
the hydrophilic fiber is exposed on a surface of the recessed part and on a surface of the tail end part, and
a lateral face of the middle part is covered with the covering material that has higher hydrophobicity than the hydrophilic fiber.

5. The tampon according to claim 1, wherein the recessed part has a flat bottom face.

6. The tampon according to claim 1, wherein the recessed part has a truncated conical shape.

7. The tampon according to claim 1, wherein the recessed part has a bottom including a plurality of recessed portions.

8. The tampon according to claim 1, wherein the leading end part further includes a plurality of recessed parts in addition to the recessed part that includes the position of the central axis of the absorbent body.

* * * * *